United States Patent [19]
Sarver et al.

[11] Patent Number: 5,868,746
[45] Date of Patent: *Feb. 9, 1999

[54] METHOD AND APPARATUS FOR SECURING ADJACENT BONE PORTIONS

[75] Inventors: David Ralph Sarver, Logansport; Barry Lynn Eppley, Indianapolis; Keith Raymond D'Alessio; William Stanley Pietrzak, both of Warsaw; Thomas Wendell Sander, Winona Lake, all of Ind.

[73] Assignee: Biomet, Inc., Warsaw, Ind.

[ * ] Notice: The term of this patent shall not extend beyond the expiration date of Pat. No. 5,569,250.

[21] Appl. No.: 736,852

[22] Filed: Oct. 28, 1996

Related U.S. Application Data

[63] Continuation of Ser. No. 204,036, Mar. 1, 1994, Pat. No. 5,569,250.
[51] Int. Cl.⁶ .................................................. A61B 17/00
[52] U.S. Cl. .............................. 606/69; 606/53; 606/72; 606/77
[58] Field of Search ................................. 606/58, 66, 67, 606/69–71, 73, 72, 77, 53

[56] References Cited

U.S. PATENT DOCUMENTS

| | | |
|---|---|---|
| 3,531,561 | 9/1970 | Trehu . |
| 3,565,066 | 2/1971 | Roaf et al. . |
| 3,636,956 | 1/1972 | Schneider . |
| 3,960,151 | 6/1976 | Kuhn . |
| 4,429,690 | 2/1984 | Angelino-Pievani . |
| 4,523,591 | 6/1985 | Kaplan et al. . |
| 4,781,183 | 11/1988 | Casey et al. . |
| 4,905,680 | 3/1990 | Tunc . |
| 5,250,584 | 10/1993 | Ikada et al. . |
| 5,275,601 | 1/1994 | Gogolewski et al. . |
| 5,413,577 | 5/1995 | Pollock . |
| 5,569,250 | 10/1996 | Sarver et al. .............................. 606/69 |
| 5,676,699 | 10/1997 | Gogolewski et al. . |

FOREIGN PATENT DOCUMENTS

| | | |
|---|---|---|
| 195455B1 | 9/1986 | European Pat. Off. . |
| 276153A2 | 7/1988 | European Pat. Off. . |
| 491983A1 | 12/1990 | European Pat. Off. . |
| 0491983A | 7/1992 | European Pat. Off. .................. 606/72 |
| 3701765C1 | 6/1988 | Germany . |
| 2140523 | 11/1984 | United Kingdom . |

OTHER PUBLICATIONS

Seth R. Thaller et al., "Use of Biodegradable Plates and Screws in Rabbit Model", *The Journal of Craniofacial Surgery*, vol. 2, No. 4, Mar. 1992, pp. 168–173.

Kirk P. Andriano et al., "Process and Characterization of Absorbable Polyactide Polymers for Use in Surgical Implants", *Journal of Applied Biomaterials*, vol. 5, 1994, pp. 133–140.

(List continued on next page.)

*Primary Examiner*—Jennifer Bahr
*Assistant Examiner*—Stephen Huang
*Attorney, Agent, or Firm*—Harness, Dickey & Pierce, P.L.C.

[57] ABSTRACT

A biocompatible osteosynthesis plate operable for being enhanced in a substantially secured relation to a plurality of adjacent bone portions is provided. The biocompatible osteosynthesis plate includes an elongated section having a top face and a bottom face, at least one fastener opening disposed between the top face and the bottom face, and means disposed upon elongated section to permit the formation of additional fastener openings therethrough during a surgical procedure. The osteosynthesis plate is in a first configuration at a first thermochemical state and is operable to be converted to a second thermochemical state so that it may be deformed prior to fixation. The osteosynthesis plate may further include means disposed upon the elongated section for enhancing structural rigidity, which may be provided as one or more raised surfaces, or rails, disposed upon the top face of the osteosynthesis plate.

21 Claims, 7 Drawing Sheets

OTHER PUBLICATIONS

K.L. Gerlach, "In–vivo and Clinical Evaluations of Poly (L–lactide) Plates and Screws for Use in Maxillofacial Traumatology", *Clinical Materials*, No. 13, 1993, pp. 21–28.

Kenneth E. Salyer et al., "A Comparative Study of the Effects of Biodegradable and Titanium Plating Systems on Cranial Growth and Structure: Experimental Study in Beagles", *Plastic and Reconstructive Surgery*, vol. 93, No. 4, 1994, pp. 705–713.

Barry L. Eppley et al., "Effects of Resorbable Fixation on Craniofacial Skeletal Growth: A Pilot Experimental Study", *The Journal of Craniofacial Surgery*, vol. 3, No. 4, Dec. 1992, pp. 190–196.

Seth R. Thaller, "Biodegradable Plates and Screws", pp. 99–113, Copyright 1995 by Mosby—Year Book, Inc., taken from *Advances in Plastic and Reconstructive Surgery*, vol. 11.

R. Ewers et al., "Bioabsorbable Osteosynthesis Materials", *Facial Plastic Surgery*, vol. 7, No. 3, 1990, pp. 206–214.

A.M. Radder et al., "Interface Reactions to PEO/PBT Copolymers (Polyactive [trademark]) After Implantation in Cortical Bone", *Journal of Biomedical Materials Research*, vol. 28, 1994, pp. 141–151.

Alan S. Litsky, "Clinical Reviews: Bioabsorbable Imlants for Othopaedic Fracture Fixation", *Journal of Applied Biomaterials*, vol. 4, 1993, pp. 109–111.

Rudolf R.M. Bos et al., "Bio–absorbable Plates and Screws for Internal Fixation of Mandibular Fractures", *Int. J. Oral Maxillfac. Surg.*, vol. 18, 1989, pp. 365–369.

Vivek Shetty et al., "Biomechanical Properties of Resorbable Poly–L–Lactide Plates and Screws: A Comparison with Traditional Systems", *Journal of Oral Maxillofacial Surgery*, vol. 49, 1991, pp. 517–518.

Rudolf R.M. Bos et al., "Resorbable Poly(L–Lactide) Plates and Screws for the Fixation of Zygomatic Fractures", *Journal of Oral Maxillofacial Surgery*, vol. 45, 1987, pp. 751–753.

J. Kilpikari et al., "Biodegradeable Polymers for Orthopedic Surgery", poaper from the 9th Annual Metting of the Society for Biomaterials, Birmingham, Alabama, Apr. 27–May 1, 1983.

P. Christel et al., "In Vivo Fate of Bioresorbable Bone Plates in Long–Lasting Poly(L–lactic) Acid", paper from the Second World Congresson Biomaterials, 10th Annual Meeting of the Society for Biomaterials, Washington, D.C., Apr. 27–May 1, 1984.

Advertisement for Leibinger, "3–D Plating System", Oswald Leibinger GMBH, 1991.

Advertisement for Storz (Maxillofacial), "The System for Keeping the Lowest Profile", SPA 4095, Rev. Oct., 1991.

Excerpt from article entitled "Rigid Fixation of Facial Osteotomies", *Clinics in Plastic Surgery*, vol. 16, No. 4, Oct. 1989, p. 667.

Rudolf R. M. Bos, "Poly(L–lactide) Osteosynthesis", Ph.D. Thesis, pp. 1–8, pre–1990.

R. Suuronen, "Biodegradable Fracture–Fixation Devices in Maxillofacial Surgery", *Int. J. Oral Maxillofac. Surg.*, vol. 22, 1993, pp. 50–57.

F.R. Rozema, "Poly (L–lactide) Implants in Repair of Defects of the Orbital Floor: An Animal Study", *Resorbable Poly (L–lactide) Bone Plates and Screws (PLLA) Tests and Applications*, pp. 51–98, reproduced from *Journal of Maxillofacial Surgery*, vol. 48, 1990, pp. 1305–1309.

Advertisement for Leibinger, "Titanium Micro System", Oswald Leibinger GMBH, 1992.

METHOD AND APPARATUS FOR SECURING ADJACENT BONE PORTIONS

This is a continuation of U.S. patent application Ser. No. 08/204,036, filed Mar. 1, 1994 now U.S. Pat. No. 5,569,250.

BACKGROUND OF THE INVENTION

This invention relates generally to medical implant devices, and more particularly to a biocompatible osteosynthesis plate that is deformable, yet dimensionally stable at its glass transition temperature, and relatively rigid at body temperature.

The repair of separated or dislocated bone fragments or segments following bone surgeries requires realignment of the separated or dislocated fragments or segments and subsequent secure fixation for promoting proper natural rejoinder of these bone fragments or segments. The presence of relative motion of the bone fragments or segments at a fracture or osteotomy location may result in irritation of the surrounding tissues, nonunion between the bone fragments, and an extension of the time of fracture healing. It is therefore desirable to accomplish as completely as possible an immobilization of the fracture or osteotomy site. This involves the relative fixation of affected bone segments relative to each other and in relation to the surrounding bone structure.

One example of an area in which such procedures are desirable is in the refixation of large area bone segments of the skull cap in neurosurgical and craniofacial operations on or through the vault of the human skull. In neurosurgical and craniofacial operations, one or more bone covers or segments of the skull are cut and removed. The operating technique employed in such operations includes the formation of several holes drilled through the cranial vault. A plurality of incisions, called connecting osteotomies, are then made between the drill holes by means of a saw which is provided with a guide device for avoiding dura mater injuries by the projection of the saw blade beyond the thickness of the skull. The number of holes drilled through the cranial vault, as well as the number of connecting osteotomies, is determined by the size, location and geometrical form of the bone cover to be lifted off. For example, if the bone cover to be removed is a triangular skull cap segment, three holes are preferably drilled at the corner points of the bone cover. The connecting osteotomies are made at the sides of a spherically curved triangle, resulting in a triangular skull cap segment which can be lifted off to carry out the further operation.

In the surgical treatment of craniofacial abnormalities, one or more bone segments of the skull cap may be removed and remodeled to achieve a desired cosmetic result before refixation in a displaced position relative to the surrounding bone. These operations serve to correct malformations of the skull cap which are present at birth, which operations are often performed during the infancy of the patient. These operations may include harvesting calvarian bone which is used to replace other bony tissues.

At the end of such procedures, the previously removed bone fragment or fragments are repositioned into their original locations, or in different desired locations, and are enhanced in a secured relation with other bone fragments removed during the surgical procedure and/or the surrounding bone portions. Known methods for providing fixation between adjacent bone portions have included the use of metallic plates of varying configurations, which are secured across osteotomies or fracture sites by metallic bone screws.

These devices have been made of biocompatible metals and metal alloys, such as commercially pure titanium, stainless steel and cobalt chrome molybdenum. Other materials and devices, such as wires, intramedullary nails or externally fixed pins have also been used to reduce bone fracture mobility and to improve the relative position of adjacent segments. The aim of fixation of adjacent bone portions is to immobilize the fracture or osteotomy sites in order to promote localized bone growth in the natural repair of the separation.

The disadvantages associated with the use of metallic and metallic alloy devices relate to the undesirable cosmetic results associated with the protrusion of these devices above the bone surface, especially in locations directly beneath the skin, that is, without any intervening soft tissue for masking the implant devices from being noticed externally. As such, the only way to remove these implant devices involves revision surgery after the localized bone area has healed. In addition, metal and metallic alloy devices often should be removed from a pediatric patient so as to prevent growth restriction.

The use of medical implant devices made from bioresorbable materials has been described in literature and these devices have the advantage of being absorbed by the body over a period of time so as to allow for bone or fibrous material to become repaired at a fracture or osteotomy site by growing into the space created between adjacent bone portions. Many bioresorbable materials have been suggested for use in fixation of adjacent bone portions. It was believed that these materials had to be extremely strong to fixate the bone portions over a relatively long period of time. This typically meant that the osteosynthesis plate had to be relatively thick and be made out of a high molecular weight oriented material such as poly L-lactic acid in which the molecular weight would exceed 250,000. See Pihlajamaki, H., et al., "Absorbable Pins of Self-Reinforced Poly-L-Lactic Acid for Fixation of Fractures and Osteotomies," *Journal of Bone and Joint Surgery*, v. 74-B, n. 6, p. 853–857, November 1992. In addition, it was believed that copolymers of glyceride and lactide were not appropriate for use in osteosynthesis plates because of a rapid loss of mechanical strength. Grijpma, D. W., et al., "Poly (L-lactide) Crosslinked with Spiro-bis-dimethylene-carbonate," *Polymer*, v. 34, n.7, 1993 at 1496.

While others suggest the use of non-reinforced materials, the molecular weight of the material had to be increased to maintain strength. In this regard, one author suggested using a non-oriented material having an average molecular weight of $10_6$. See Bos, R. R. M., et al., "Late Complications Related to Bioresorbable Poly (L-Lactide) Plate—Osteosyntheses", *Journal of Oral Maxillofacial Surgery*, Supp. 3, 51(a) 1993 at 190. However, there were certain problems which were associated with these particular osteosynthesis plates. First, such osteosynthesis plates tended to have a relatively high degree of inflammatory response and therefore often had to be removed from the patient. See, Bostman, O., "Current Concepts Review—Absorbable Implants for the Fixation of Fractures," *Journal of Bone and Joint Surgery*, pp. 148–153, 1991. In addition, the osteosynthesis plates had to be made relatively thick so as to provide the requisite strength, which tended to make the osteosynthesis plates have an unwanted cosmetic appearance when implanted.

A need therefore exists for a bioresorbable fastening device for bone fixation, such as an osteosynthesis plate, that is thin enough and of a suitable material to be resorbed over a desired period of time, yet is of sufficient strength to maintain relative bone fixation over the time period needed for the natural repair of fractures or osteotomies between adjacent bone portions. A need also exists for a bioresorbable osteosynthesis plate which does not produce a substantial inflammatory response. In addition, a need also exists for such a bioresorbable device to be deformable, yet dimensionally stable at temperatures above the glass transition temperature of the material from which the device is made to facilitate shaping. A need further exists for such a bioresorbable device to allow for the formation of one or more additional fastener openings at one or more required precise locations during a surgical procedure.

SUMMARY OF THE INVENTION

An advantage of the present invention is to provide a low profile biocompatible implant of sufficient strength to be operable for enhancing a substantially secured relation between a plurality of adjacent bone portions.

Another advantage of the present invention is to provide a biocompatible implant that is bioresorbable over a desired period of time while not generating a substantial inflammatory response.

A further advantage of the present invention is to provide a biocompatible implant that is relatively rigid at a first thermochemical state and is relatively deformable at a second thermochemical state to which the implant is temporarily brought prior to implantation.

Another advantage of the present invention is to provide a biocompatible implant with openings for the insertion of surgical fasteners therethrough, while allowing means to permit the formation of additional fastener openings therethrough during a surgical procedure at the surgeon's discretion.

A further advantage of the present invention is to provide a biocompatible implant that is repetitively deformable by repetitively converting the implant between a first thermochemical state and a second thermochemical state prior to implantation.

Another advantage of the present invention is to provide a biocompatible implant that can be easily and inexpensively manufactured with reduced internal stresses.

A further advantage of the present invention is to provide a biocompatible fixation device that is operable to enhance a secured relation between a biocompatible implant device and one or more adjacent bone portions.

The present invention, in one form thereof, provides a low-profile biocompatible osteosynthesis plate operable for being enhanced in a substantially secured relation to a plurality of adjacent bone portions. The osteosynthesis plate includes an elongated section having a top face and a bottom face, which elongated section is operable for traversing a fracture site or osteotomy site for subsequent fixation to adjacent bone portion. The osteosynthesis plate further includes a plurality of fastener openings disposed between the top face and bottom face to allow the traverse of a plurality of surgical fasteners therethrough. The osteosynthesis plate further includes means disposed upon the elongated section to permit the formation of additional fastener openings therethrough during a surgical procedure at the discretion of the surgeon. The osteosynthesis plate is relatively rigid at a first temperature and is deformable in three dimensions, yet dimensionally stable, at a second temperature that is above the first temperature, and is above the glass transition temperature of the plate material. The osteosynthesis plate retains a deformed position upon returning to the first temperature, but can be subsequently returned to its original configuration by subsequently returning the osteosynthesis plate to the second temperature. As such, the osteosynthesis plate of the present invention may be repeatedly deformed and returned to its original configuration in order to contour the osteosynthesis plate precisely to a desired configuration through successive iterations.

The invention, in another form thereof, provides a low-profile biocompatible osteosynthesis plate including an elongated section having a top face and a bottom face, a plurality of fastener openings disposed between the top face and the bottom face, and means disposed upon the elongated section for enhancing structural rigidity of the osteosynthesis plate. The means for enhancing structural rigidity are provided as one or more raised surfaces or "rails" which are disposed in one or more directions upon the top surface of the osteosynthesis plate for providing additional strength while adding a minimum of additional material to the plate itself. As before, this osteosynthesis plate is also able to be repetitively deformed in three dimensions by conversion to a second temperature in successive iterations until a desired contour is achieved.

The present invention also includes bioresorbable fixation devices, or bone screws, that are operable to be inserted through fastener openings disposed within the osteosynthesis plates of the present invention. As such, the present invention contemplates a bone stabilization device including a bioresorbable osteosynthesis plate and bioresorbable surgical fasteners.

The present invention also provides a composite bone stabilization device for enhancing a secured relation between a plurality of adjacent bone portions through the combination of a bioresorbable osteosynthesis plate and metallic or metallic alloy surgical fasteners.

The present invention also provides a method for forming a low-profile biocompatible osteosynthesis plate including the steps of formation of a sheet stock, polymer testing, formation of an osteosynthesis plate from a sheet stock, removal of surface irregularities, ultrasonic surface cleaning, sterilization and packaging.

The present invention also provides a method for enhancing a substantially secured relation between a plurality of adjacent bone portions with reduced bone surface protrusion including the steps of providing a low-profile biocompatible osteosynthesis plate, positioning the biocompatible osteosynthesis plate upon a plurality of adjacent bone portions, providing a plurality of surgical fasteners for enhancing a fixed relation between the osteosynthesis plate and at least one adjacent bone portion, positioning the plurality of surgical fasteners within a plurality of fastener openings upon the osteosynthesis plate and substantially securing the plurality of surgical fasteners into the adjacent bone portions.

BRIEF DESCRIPTION OF THE DRAWINGS

Other advantages of the present invention will become apparent to one skilled in the art upon reading the following specification and the following drawings.

DETAILED DESCRIPTION OF THE PREFERRED EMBODIMENT

It should be understood that while this invention is described in connection with a particular example, the scope of the invention need not be so limited. Rather, those skilled in the art will appreciate that the following teachings can be used in a much wider variety of applications than the examples specifically mentioned herein.

Figure 1A:
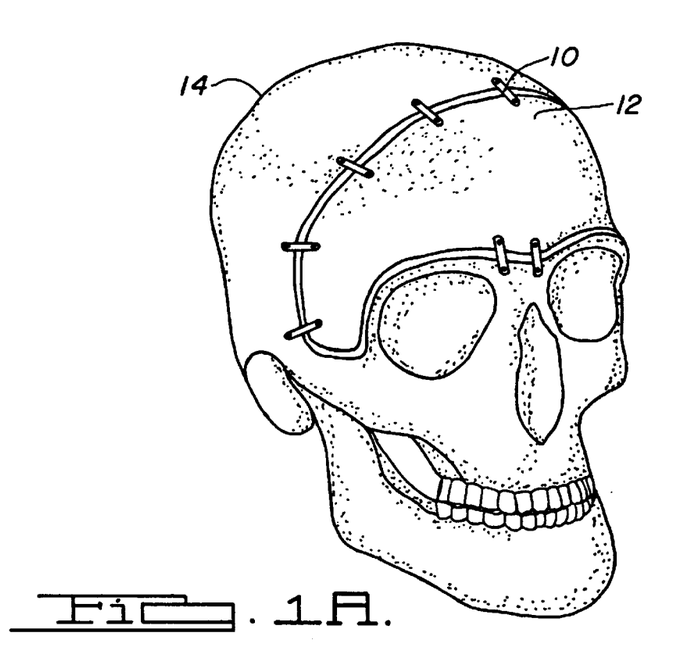
FIG. 1A is a perspective view illustrating a plurality of osteosynthesis plates according to the teachings of the preferred embodiment of the present invention shown in association with an anterior craniosynostosis of a human skull.

Referring now to FIG. 1A, there is shown a biocompatible osteosynthesis plate 10 according to a preferred embodiment of the present invention. The biocompatible osteosynthesis plate 10 is shown as being disposed between a bone segment 12, such as that removed during a surgical procedure, and a skull 14. It will be appreciated that the biocompatible osteosynthesis plate 10 may be of any size or shape as will be hereinafter discussed, and may be a bioresorbable implant. Further, the biocompatible osteosynthesis plate 10 may also be deformable at one particular thermochemical state but is relatively rigid at another thermochemical state. A "thermochemical state" as used in describing the present invention is defined as a combination of thermal and chemical conditions resulting from exposure to certain thermal and chemical environments. Although one type of change in thermochemical state occurs by a change of temperature alone, changes in thermochemical state of a biocompatible implant of the present invention should be understood as not limited only to changes in temperature.

Preferably, the biocompatible osteosynthesis plate 10 is relatively rigid at both room temperature and at human body temperature, but is deformable at temperatures above the glass transition temperature of the material from which the biocompatible osteosynthesis plate 10 is made. When heated above the glass transition temperature, the biocompatible osteosynthesis plate 10 preferably converts from a relatively rigid solid to a relatively rubbery solid that is easily deformable in three dimensions.

Importantly, the biocompatible osteosynthesis plate 10 is formed by a method such that the biocompatible osteosynthesis plate 10 is dimensionally stable at the glass transition temperature of the material from which the plate 10 is made. As used herein, the term "dimensionally stable" means that the biocompatible osteosynthesis plate 10 is able to retain substantially the same configuration at either of two thermochemical states so that the osteosynthesis plate 10 may be shaped a number of different times in the manner described below. This dimensional stability is due to the fact that the internal stresses in the osteosynthesis plate 10 are minimized by the way in which the osteosynthesis plate 10 is manufactured which is also discussed below. In addition, the material used for the osteosynthesis plate 10 is preferably a bioabsorbable polymer which has adequate retention of strength but does not exhibit an inflammatory reaction. Typically, this requires a strength retention of about 65% up to a period of from about 6 to 8 weeks from implantation and substantially complete resorption after a period of about one year.

The biocompatible osteosynthesis plate 10 is preferably formed from a non-reinforced lactide and glyceride copolymer composition which is non-oriented and has a glass transition temperature of between 55° C. and 62° C. The copolymer is made from about 70–85% m lactide moieties and from about 15–30% m glyceride moieties having a molecular weight $M_n$ of generally between 30,000 and 100,000. Typically from about 30,000 to about 80,000 molecular weight copolymer is used. However, the preferred molecular weight of the copolymer is from about 40,000 to about 60,000. As used herein, the molecular weight of the copolymer is related to the intrinsic viscosity of the copolymer according to Schindler's formula which, under the present circumstances, is as follows:

$$[n]=5.45\times10^{-4}(M_n)^{0.73}$$

where
[n]=intrinsic viscosity
$M_n$=molecular weight

See Schindler and Harpen, D., "Polylactide II. Viscosity-Molecular Weight Relationships and Underperturbed Chain Dimensions," *Journal of Polymer Science: Polymer Chemistry Edition*, v. 17, 2593–2594 (1979). It will also be appreciated that intrinsic viscosity may also be related to inherent viscosity in the manner described in Soloman, O. F. and Ciuta, I. Z., "Determination de la Viscosité Intrinséque de Solutions de Polyméres par une Simple Détermination de la Viscosité," Journal of Applied Polymer Science, v. VI, n. 24, p. 683–686 (1962).

Others have indicated that such glyceride copolymers did not have sufficient strength for use as osteosynthesis plates. Grijpma, D. W., et al., "Poly (L-lactide) crosslinked with spiro-bis-dimethylene-carbonate," *Polymer*, v. 34, n.7, 1993 at 1496. In addition, others have suggested that a higher molecular weight material should be used to form osteosynthesis plates so as to maintain the strength of the plate. See Bos, R. R. M., et al., "Late Complications Related to Bioresorbable Poly (L-Lactide) Plate—Osteosyntheses", *Journal of Oral Maxillofacial Surgery*, Supp. 3, 51(a) 1993 at 190. However, Applicants have determined that it is critical in certain aspects of the present invention to use the aforementioned material with a molecular weight $M_n$ of between 30,000 and 100,000 to obtain the above properties. An osteosynthesis plate 10 made using this material and in the manner discussed below will retain a substantial proportion of its strength after the first several weeks following implantation when this strength must be relatively high, yet will be resorbed relatively rapidly. This fact, together with the fact that osteosynthesis plate 10 preferably has a crystallinity of less than 10%, causes the osteosynthesis plate 10 to be less susceptible to an inflammatory response which was associated with the prior art. Further, because the osteosynthesis plate 10 is made from this material, the osteosynthesis plate 10 is operable stabilize a plurality of bone portions for a period of about four to eight weeks following implantation and yet be completely resorbed within about a year following implantation. In addition, the relatively fast resorption of this material reduces the unwanted cosmetic appearance associated with the prior art as well as growth restriction which was also associated with the prior art. It will be understood, however, that other suitable materials may be used which have the advantageous properties discussed above.

Figure 1B:
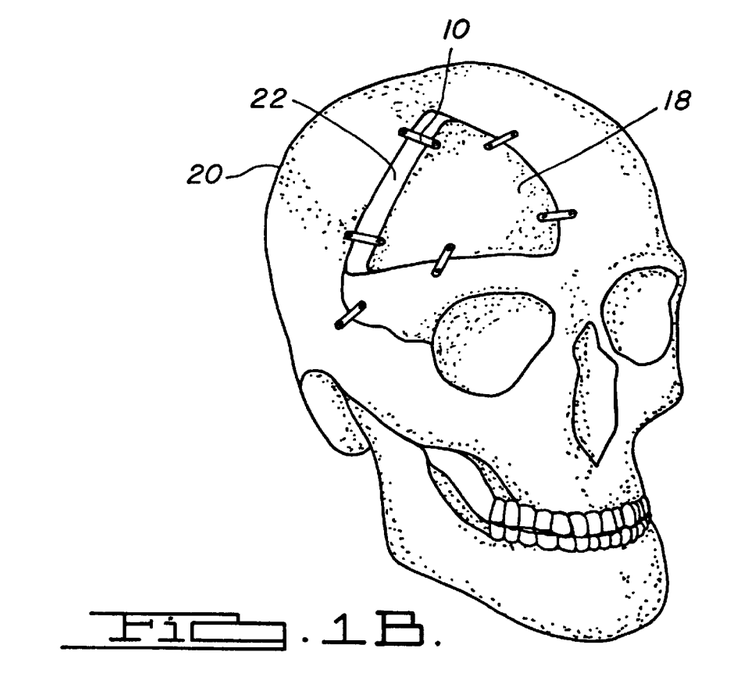
FIG. 1B is a perspective view illustrating a plurality of osteosynthesis plates according to the teachings of a preferred embodiment of the present invention shown in association with a plagiocephaly of a human skull.

The environment shown in FIG. 1A is indicative of a typical refixation procedure, whereby a bone segment 12 is enhanced in a substantially secured relation to the skull 14 by a plurality of biocompatible osteosynthesis plates 10 following a bifrontal craniotomy surgical procedure. Referring now to FIG. 1B, there are shown a plurality of biocompatible osteosynthesis plates according to a preferred embodiment of the present invention. The biocompatible osteosynthesis plates 10 are disposed to enhance a substantially secured relation between a bone flap 18 and the surrounding regions of the skull 20. FIG. 1B illustrates a typical placement of the bone flap 18 as it occurs during an infant craniosynostosis, wherein deformations in the skull 20 are corrected through a surgical procedure which involves removal of a section of the skull 20, and a reshaping of that section to form a bone flap 18 that can be subsequently enhanced in a secured relation to the skull 20 using the biocompatible osteosynthesis plates 10 of the present invention. In this type of surgical procedure, it is common to have a gap 22 between the bone flap 18 and the skull 20 in one direction. In such a situation, the biocompatible osteosynthesis plates 10 are operable to traverse this gap 22 to be enhanced in a secured relation between the bone flap 18 and the surrounding skull 20.

It will be appreciated that the biocompatible osteosynthesis plates 10 may be of a variety of sizes and/or shapes as hereinafter discussed and may also be of a bioresorbable material as discussed above. In addition, the biocompatible osteosynthesis plate 10 is preferably relatively rigid at both room temperature and at human body temperature, but is deformable at temperatures above the glass transition temperature of the material from which the biocompatible osteosynthesis plate 10 is made. When heated above the glass transition temperature, the biocompatible osteosynthesis plate 10 preferably converts from a relatively rigid solid to a relatively rubbery solid that is easily deformable in three dimensions. Importantly, the biocompatible osteosynthesis plate 10 is also dimensionally stable at its glass transition temperature.

Figure 1C:
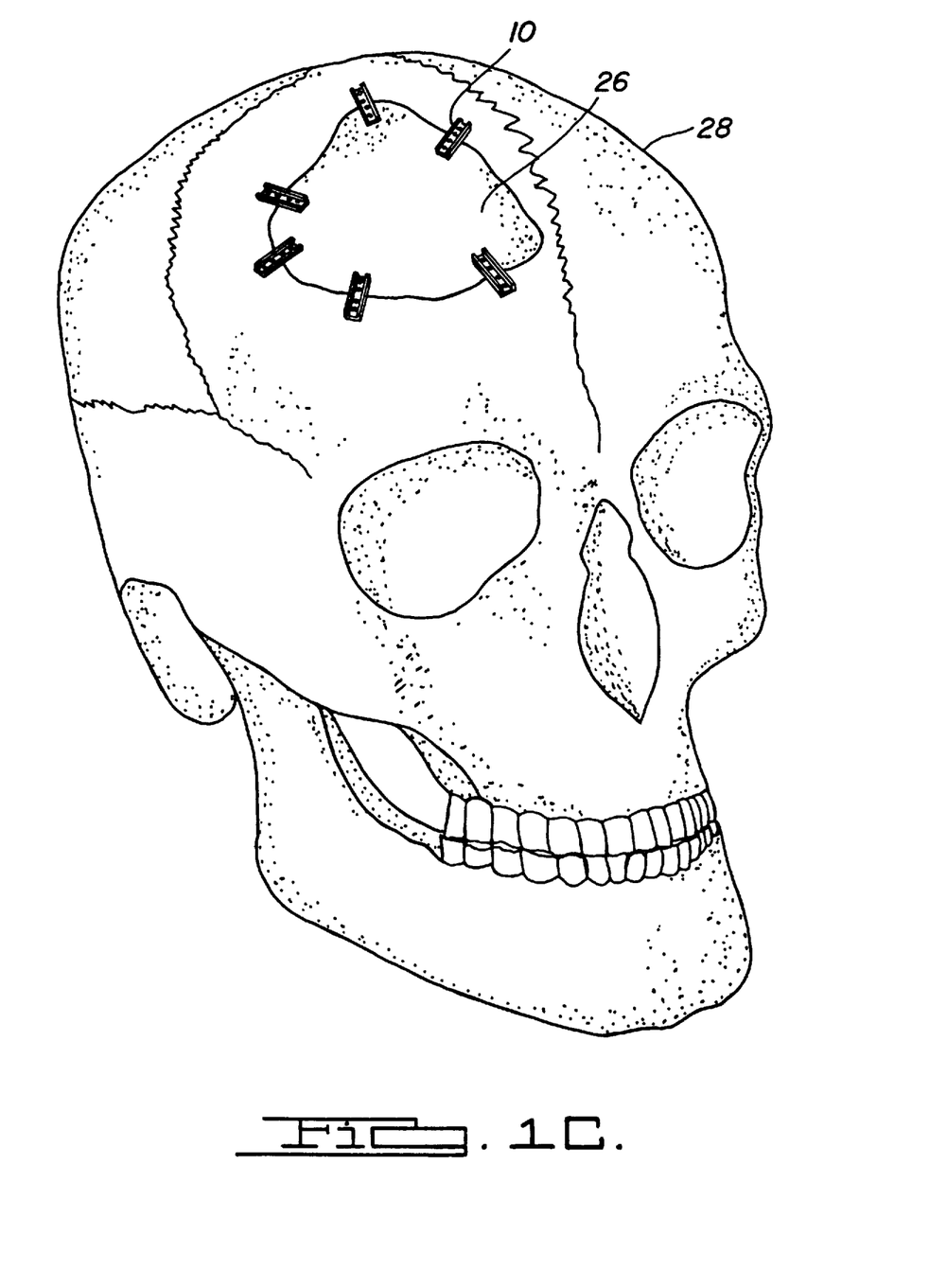
FIG. 1C is a perspective view illustrating a plurality of osteosynthesis plates according to the teachings of a preferred embodiment of the present invention shown in association with the repair of a bone flap upon a human skull.

Referring now to FIG. 1C, there are shown a plurality of biocompatible osteosynthesis plates 10 of a different shape that are disposed to enhance a secured relation between a bone flap 26 and the surrounding portions of the skull 28 following the removal of the bone flap 26 during a surgical procedure, as previously described. The biocompatible osteosynthesis plates 10 may be of any size or shape as will be hereinafter described and may also be made from the same materials and may also have the same characteristics as described before.

Figure 1D:
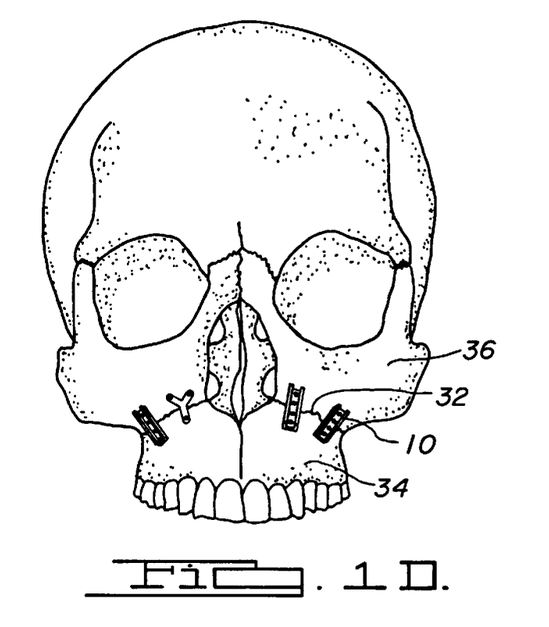
FIG. 1D is a frontal view of a plurality of osteosynthesis plates according to the teachings of a preferred embodiment of the present invention shown in association with the repair of the nasomaxillary and zygomatic buttresses of the maxillofacial region of a human skull.

Referring now to FIG. 1D, there are shown a plurality of biocompatible osteosynthesis plates 10 that are disposed across a plurality of bone fractures 32. In this illustration, the bone fractures 32 are in the form of mid-face fractures, such as LeFort I Fractures or osteotomies of the craniofacial skeleton, with the biocompatible osteosynthesis plates 10 being used to reestablish the nasomaxillary buttresses 34 and zygomatic buttresses 36. As can be seen from FIG. 1D, the biocompatible osteosynthesis plates 10 can take on a variety of shapes, as will be discussed below, and may also be constructed in a variety of sizes suitable for the particular need. The biocompatible osteosynthesis plates 10 may also be made from the same materials and may also have the same characteristics as described before.

Figure 1E:
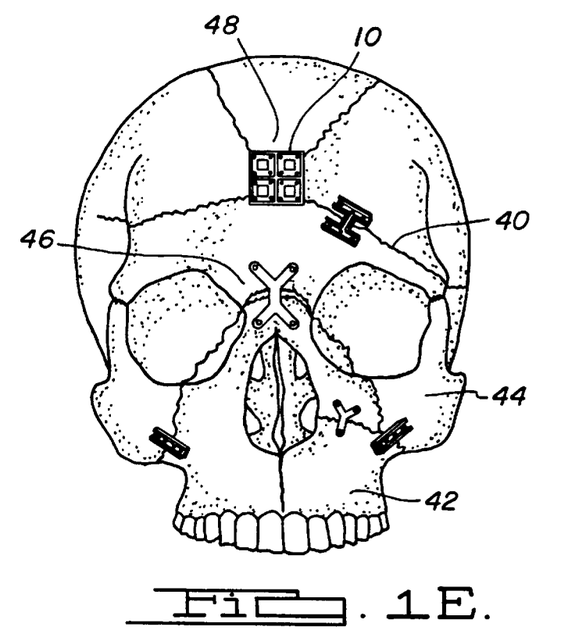
FIG. 1E is a frontal view of a plurality of osteosynthesis plates according the teachings of a preferred embodiment of the present invention shown in association with the repair of multiple maxillofacial fractures.

Referring now to FIG. 1E, there are shown a plurality of biocompatible osteosynthesis plates 10 of yet another geometric shape disposed to enhance a substantially secured relation across a plurality of bone fractures 40. These biocompatible osteosynthesis plates 10 are shown in this illustration to reestablish continuity at the nasomaxillary buttresses 42, the zygomatic buttresses 44, the nasal region 46 and at the metopion 48. The biocompatible osteosynthesis plates 10 may be of any size or shape as will be hereinafter described and may also be made from the same materials and may also have the same characteristics as described before.

Figure 2:
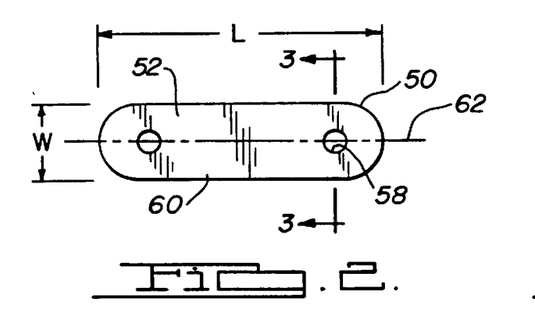
FIG. 2 is a top view of an osteosynthesis plate according to the teachings of a preferred embodiment of the present invention.
Figure 3:
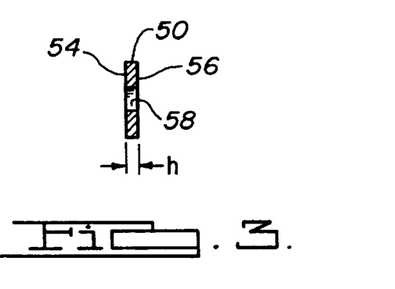
FIG. 3 is a cross-sectional view of an osteosynthesis plate of FIG. 2 along line 3—3 according to the teachings of a preferred embodiment of the present invention.

Referring now to FIGS. 2 and 3, there is shown a biocompatible osteosynthesis plate in the form of a flat plate 50. The flat plate 50 includes an elongated section 52 having a top face 54 and a bottom face 56. The flat plate 50 is further shown to include a plurality of fastener openings 58 that are of substantially cylindrical shape and are disposed between the top face 54 and the bottom face 56. The fastener openings 58 are operable to allow the traverse of surgical fasteners for enhancing a secured relation between the flat plate 50 and a bone surface (not shown) to which the flat plate 50 may be applied. It will be appreciated, however, that the fastener openings 58 do not have to be present if there are other means for securing the flat plate 50 to bone. Preferably, the flat plate 50 is applied to a bone surface such that the plane or contour formed by the bottom face 56 is substantially flush with the bone surface to which the flat plate 50 is applied.

The flat plate 50 further includes means disposed upon the elongated section 52 to permit the formation of additional fastener openings therethrough at a plurality of different positions during a surgical procedure. In a preferred embodiment, this is provided by having the elongated section 52 include a mid-portion 60 which is disposed between the fastener openings 58 and have substantially the same width as the portion of the flat plate 50 which is adjacent to the fastener openings 58. Accordingly, the surgeon is able to drill through the mid-portion 60 to form additional fastener openings as the particular application requires. It will be noted that additional fastener openings may be formed either on the axis of the elongated section 52 or off the axis of the elongated section 52. The presence of the mid portion 60 serves to distinguish this flat plate 50 from other osteosynthesis plates which may be widened only in the region of the fastener openings formed thereon, with the remainder of the osteosynthesis plate being of a more narrow configuration, and therefore not suitable for the formation of additional fastener openings.

The flat plate 50 is provided to be in a "low-profile" construction, that is, of a preferably thin nature so as to cause a minimum protrusion above the bone surface to which it is applied. In this regard, the term "low profile" will be used to refer to a construction in which the width is greater than about six times the height of the central region of the plate 50. For example, the plate 50 may typically have a width ("w") of 0.156", a length ("l") of between about 0.454" to 0.75", and a height ("h") of 0.02" as shown in FIG. 2. The flat plate 50 is further provided to be preferably of a bioresorbable material, such that the flat plate 50 may be resorbed into the body through processes well known to those skilled in the art over a desired period of time. In this regard, the flat plate 50 may be formed from one of the materials described above.

The flat plate 50 is also characterized by its ability to be deformed during a surgical procedure to be conformed to the contour of the bone surface to which it is applied. This feature is especially useful in the surgical repair of bone surfaces having high curvatures, including the maxillofacial bones of the craniofacial skeleton.

During such deformation, the flat plate 50 is converted from a first thermochemical state to a second thermochemical state, as described previously, and retaining a deformed condition following a return to the first thermochemical state. Preferably, this deformation is accomplished quickly and conveniently by simply heating the flat plate 50 in a heat pack (not shown) or other suitable heating device and manipulating the plate. One such heating device is described in U.S. Pat. No. 5,263,991 which is hereby incorporated by reference. More preferably, because the flat osteosynthesis plate 50 is formed by a method which causes the plate to be dimensionally stable, the flat plate 50 is able to return to its original configuration upon reconverting the flat plate 50 to the second thermochemical state. As such, it will be appreciated that this ability allows the flat plate 50 to be repetitively converted, deformed and returned to its original configuration, thus allowing for successive attempts by a surgeon during a surgical procedure to conform the flat plate 50 in three dimensions to correspond as closely as possible to the contours of the bone surface to which the flat plate 50 will be applied.

The formation of additional fastener openings through the flat plate 50 may be accomplished by simply drilling through the material from which the flat plate 50 is made as discussed above. Such drilling is performed through means well known to those skilled in the art. The flat plate 50 is then operable to accept a plurality of surgical fasteners, such as biocompatible or bioresorbable bone screws, which may be constructed of the same material as the flat plate 50, or may alternatively be made of a metallic or metallic alloy material such as commercially pure titanium, stainless steel or cobalt chrome molybdenum. It will be appreciated that other suitable materials for the surgical fasteners may also be used in conjunction with the flat plate 50. As such, a combination bone stabilization device involving the use of a bioresorbable form of the flat plate 50 in combination with surgical fasteners made of a metallic or metallic alloy material is contemplated, as well as an entirely bioresorbable bone stabilization device, wherein both the flat plate 50 and the surgical fasteners inserted therethrough are provided as bioresorbable materials. It will be appreciated, however, that if the flat plate 50 is secured to bone using an adhesive, the fastener openings need not be formed.

The positioning of the flat plate 50 is preferred to be with its bottom face 56 in substantially flush contact with the bone surface to which it is applied, and with a plurality of fasteners (not shown) disposed therethrough to an enhanced secured position, wherein the head of the surgical fastener is tightened against the top face 54 of the flat plate 50. This arrangement results in an enhanced secured relation between the flat plate 50 and the underlying bone surface.

Figures 4, 5:
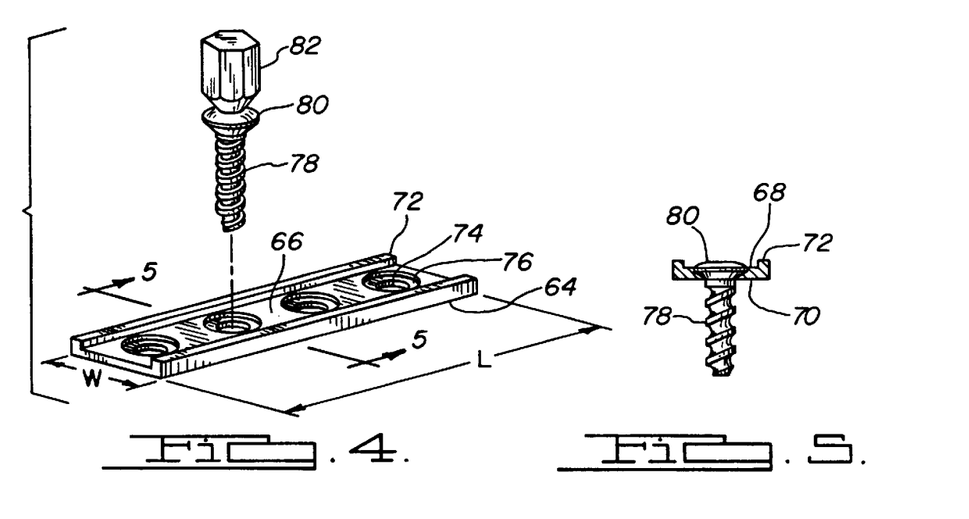
FIG. 4 is a perspective view illustrating an osteosynthesis plate including a plurality of rails for enhancing structural rigidity of the osteosynthesis plate, in combination with a bone screw positioned in a relative elevated position for insertion within a fastener opening of the osteosynthesis plate.
FIG. 5 is a cross-sectional view of the osteosynthesis plate shown in FIG. 4 along line 5—5, with a bone screw disposed within a fastener opening of the osteosynthesis plate.

Referring now to FIGS. 4 and 5, there is shown a biocompatible railed osteosynthesis plate 64 according to a preferred embodiment of the present invention. FIG. 4 illustrates a perspective view of the railed osteosynthesis plate 64, which includes an elongated section 66 having a top face 68 and a bottom face 70. The railed osteosynthesis plate 64 is further shown to include a means disposed upon the elongated section 66 for enhancing the structural rigidity of the railed osteosynthesis plate 64. Preferably, this is provided as at least one protrusion of material disposed upon the top face 68 in the form of a pair of longitudinal rails 72 disposed along the length of the railed osteosynthesis plate 64 along the edges of the top face 68. It will be appreciated that the means for enhancing structural rigidity may also be provided by other configurations of protruding material disposed along the surface of the railed osteosynthesis plate 64. It will also be noted that the rails 72 may be provided in any suitable configuration and in any direction for preventing longitudinal and torsional bending of the railed osteosynthesis plate 64. Also, the rails 72 may be provided in a discontinuous or undulating configuration, so as to allow for the specific surface requirements, such as the connection of or interaction between multiple osteosynthesis plates, which may be joined to one another through overlapping two or more plates and installing a surgical fastener between concentric overlapping fastener openings. The plate 64, for example, typically has a width of about 0.27", a length (l) of between about 0.834" to 1.586" and a height of about 0 0.055" at the rails and of about 0.025" between the rails.

This type of configuration of osteosynthesis plate is intended to render the plate 64 in a "low-profile" configuration. This is accomplished by providing the elongated section 66 to be as thin as possible to accomplish the desired result, while being reinforced by protrusions which add a minimum amount of material to the railed osteosynthesis plate 64 for accomplishing enhanced structural rigidity. Preferably, the width of the osteosynthesis plate 64 is greater than approximately six times the height of the central region of the elongated section 66. It has been determined that a minimum of additional material is desirable for minimizing the amount of mass and the cross-section of the osteosynthesis plate 64, as well as providing the desired resorption time for a complete resorption of the osteosynthesis plate 64 into the body. It has also been determined that this principle, which involves the spreading of the mass of an osteosynthesis plate over a larger surface area, provides improved results in both reducing the cosmetic effect of implantation of these devices, as well as providing a more favorable time for resorption of the material due to smaller cross-sectional area. The railed osteosynthesis plate 64 may preferably be of a bioresorbable material as described above and be dimensionally stable.

The railed osteosynthesis plate 64 is also characterized by its ability to be deformed during a surgical procedure to be conformed to the contour of the bone surface to which it is applied. This feature is especially useful in the surgical repair of bone surfaces having high curvatures, including the maxillofacial bones of the skull, as previously described.

The railed osteosynthesis plate 64 also includes a plurality of fastener openings 74 which are disposed between the top face 68 and the bottom face 70. As before, the fastener openings 74 are operable to allow the traverse of a plurality of surgical fasteners therethrough. The fastener openings 74 may each be further provided with a countersink 76 which is operable to accept a preferably correspondingly shaped portion of a head of a surgical fastener. As such, the countersink 76 may be oriented in a substantially hemispherical configuration, a substantially frustoconical configuration, or in any other configuration suitable for the particular need.

FIGS. 4 and 5 also illustrate a surgical fastener in the form of a bone screw 78 located above the surface of the railed osteosynthesis plate 64 in FIG. 4, and located in its fully inserted position in FIG. 5. When fully inserted, the head 80 of the bone screw 78 may be substantially contained between the rails 72 thereby complementing the low-profile configuration of the railed osteosynthesis plate 64. The bone screw 78 may be made from the same biocompatible or bioresorbable material as the railed osteosynthesis plate 64, thereby providing a fully bioresorbable bone stabilization device. The bone screw 78 may also be provided as a metallic or metallic alloy, including commercially pure titanium, stainless steel and cobalt chrome molybdenum, thereby providing a composite bone stabilization device with a resorbable osteosynthesis plate and nonresorbable fasteners.

As is illustrated in FIG. 4, when the surgical fastener is provided in the form of a bioresorbable bone screw 78, the bone screw 78 includes a fastener extension 82 disposed in communication with the screw 80. The fastener extension 82 is operable to provide a convenient means for engaging the bone screw 78 for insertion within a fastener opening 74 and subsequent rotation of the bone screw 78 while threading into an underlying bone structure. The fastener extension 82 is operable to be detached from the head 80 by the exertion of torque beyond that necessary for threading and tightening of the bone screw 78 into the underlying bone structure. As such, once the bone screw 78 is in a substantially tightened condition against the osteosynthesis plate 64 and the underlying bone structure, the exertion of additional torque will shear the material at the interface between the fastener extension 82 and the head 80. The fastening extension 82 may be provided in a hexagonal shape so as to be engaged by a corresponding hexagonal shaped device, although it will be appreciated that the fastener extension 82 may be shaped in any suitable configuration to match any type of engagement device. When the bone screw 78 is made from a bioresorbable material, the osteosynthesis plates described herein preferably have the countersinks 76 in the fastener openings 74 as shown in FIG. 4. When the bone screw 78 is made of metal or a metal alloy, the osteosynthesis plates preferably do not have the countersinks 76 in the fastener openings 74.

Figure 6A:
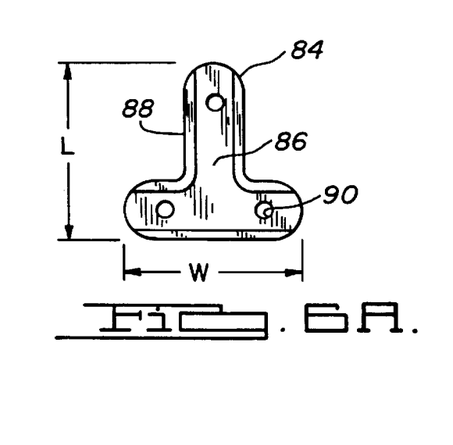
FIG. 6A is a top view illustrating a railed T-osteosynthesis plate according to the teachings of a preferred embodiment of the present invention.
Figure 6B:
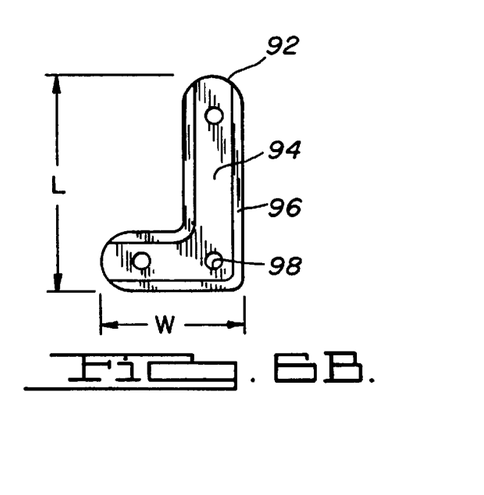
FIG. 6B is a top view illustrating a railed L-osteosynthesis plate according to the teachings of a preferred embodiment of the present invention.

Referring now to FIGS. 6A through 6L, there are shown a plurality of configurations of osteosynthesis plates according to the present invention. In this regard, a railed T-plate 84 is shown in FIG. 6A. The railed T-plate 84 includes an elongated section 86 upon which are located a plurality of rails 88. The rails 88 are shown to be disposed along the edges of the elongated section 86 at all locations except the terminal portions of the railed T-plate 84. The railed T-plate 84 is further shown to include a plurality of fastener openings 90 disposed through the elongated section 86. A typical railed T-plate 84 has a width of about 0.644", a length (l) 0.833" and a height at the rails of about 0.055" and of about 0.025" between the rails. FIG. 6B shows a railed L-plate 92 according to the present invention. The railed L-plate 92 is shown to include an elongated section 94 upon which are located a plurality of rails 96. The rails 96 are disposed on all edges of the elongated section 94 except for the terminal portions of the railed L-plate 92. The railed L-plate 92 is further shown to include a plurality of fastener openings 98 disposed upon the elongated section 94 near the terminal portions and at the corner section of the elongated section 94. A typical railed L-plate 92 has a width of about 0.456", a length (l) of about 0.834" and a height at the rails of about 0.055" and of about 0.025" between the rails.

Figure 6C:
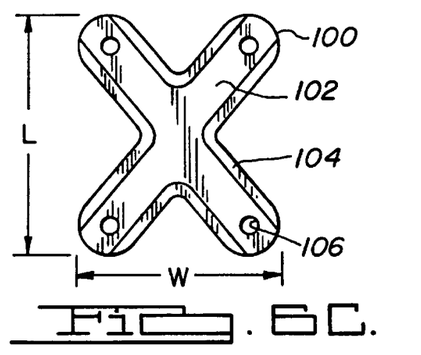
FIG. 6C is top view illustrating a railed X-osteosynthesis plate according to the teachings of a preferred embodiment of the present invention.

Referring now to FIG. 6C, there is illustrated a railed X-plate 100 having an elongated section 102 upon which are located a plurality of rails 104. The rails 104 are disposed on the edges of the elongated section 102, except for the terminal portions of the railed X-plate 100. The railed X-plate 100 is further shown to include a plurality of fastener openings 106 disposed at the terminal portions of the railed X-plate 100. A typical railed X-plate 100 has a width of about 0.642", a length (l) of about 0.795" and a height at the rails of about 0.055" and of about 0.025" between the rails.

Figure 6D:
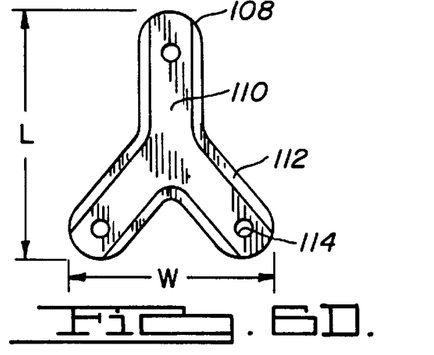
FIG. 6D is a top view illustrating a railed Y-osteosynthesis plate according to the teachings of a preferred embodiment of the present invention.
Figure 6E:
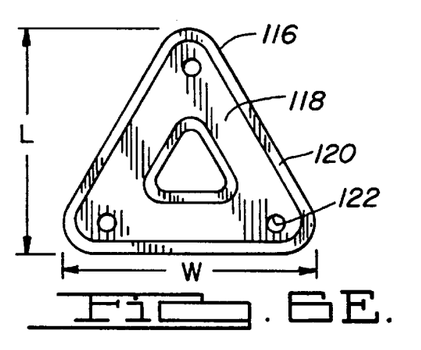
FIG. 6E is a top view illustrating a railed triangle osteosynthesis plate according to the teachings of a preferred embodiment of the present invention.

A railed Y-plate 108 is shown in FIG. 6D, which includes an elongated section 110 upon which are located a plurality of rails 112. The rails 112 disposed about the edges of the railed Y-plate 108, except at the terminal locations of the railed Y-plate 108. The railed Y-plate 108 is further shown to include a plurality of fastener openings 114 located at the terminal portions of the railed Y-plate 108. A typical railed Y-plate 108 has a width of about 0.642", a length (l) of about 0.818" and a height at the rails of about 0.055" and of about 0.025" between the rails. A railed triangle plate 116 is shown in FIG. 6E which has an elongated section 118, upon which are disposed a plurality of rails 120 about the periphery of the railed triangle plate 116. The railed triangle plate 116 is further shown to include a plurality of fastener openings 122 located at the angle portions of the triangle shape. A typical railed triangle plate 116 has a width of about 0.646", a length (l) of about 0.581" and a height at the rails of about 0.055" and of about 0.025" between the rails.

Figure 6F:
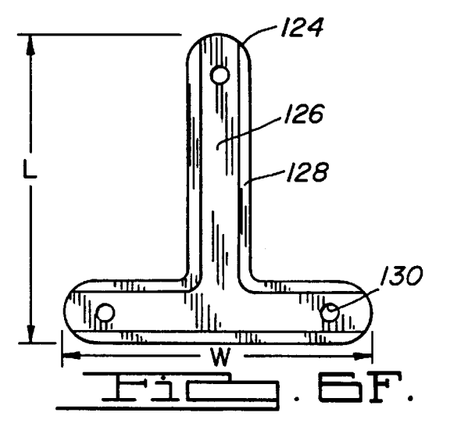
FIG. 6F is a top view illustrating a large railed T-osteosynthesis plate according to the teachings of a preferred embodiment of the present invention.
Figure 6G:
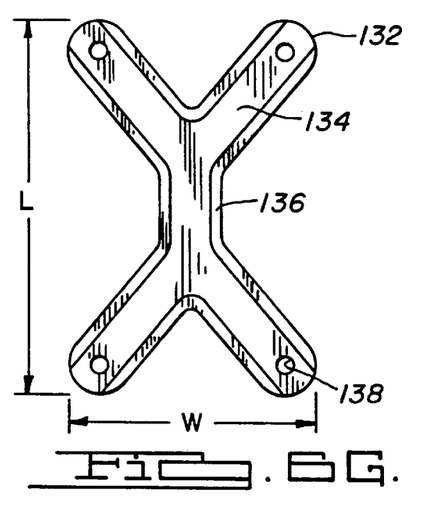
FIG. 6G is a top view illustrating a large railed X-osteosynthesis plate according to the teaching of a preferred embodiment of the present invention.

Referring now to FIG. 6F, there is shown a large railed T-plate 124, including an elongated section 126 upon which are disposed a plurality of rails 128. The long railed T-plate 124 includes a plurality of fastener openings 130 located at the terminal portions of the T-shape. A typical large railed T-plate 124 has a width of about 1.162", a length (l) of about 1.018" and a height at the rails of about 0.055" and of about 0.025" between the rails. Referring to FIG. 6G, there is shown a large railed X-plate 132 having an elongated section 134 upon which are located a plurality of rails 136. The large railed X-plate 132 includes a plurality of fastener openings 138 located at the terminal portions of the X-shape. A typical large railed X-plate 132 has a width of about 0.642", a length (l) of about 0.99" and a height at the rails of about 0.055" and of about 0.025" between the rails.

Figure 6H:
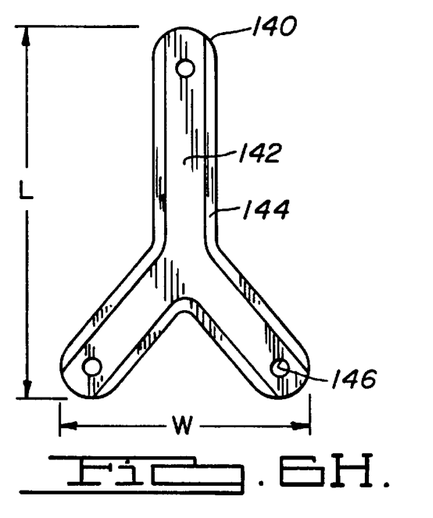
FIG. 6H is a top view illustrating a large railed Y-osteosynthesis plate according to the teachings of a preferred embodiment of the present invention.
Figure 6I:
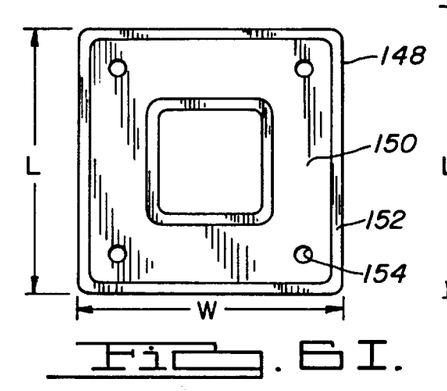
FIG. 6I is a top view illustrating a railed square osteosynthesis plate according to the teachings of a preferred embodiment of the present invention.
Figure 6J:
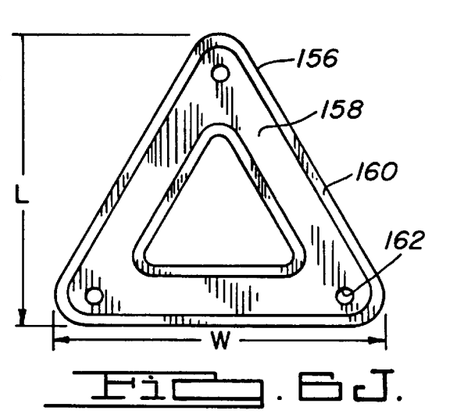
FIG. 6J is a top view illustrating a large railed triangle osteosynthesis plate according to the teachings of a preferred embodiment of the present invention.

FIG. 6H illustrates a large railed Y-plate 140 having an elongated section 142 upon which are located a plurality of rails 144. The large railed Y-plate 140 is further shown to include a plurality of fastener openings 146 disposed at the terminal portions of the large Y-shape. A typical large railed Y-plate 140 has a width of about 0.790", a length (l) of about 1.162" and a height at the rails of about 0.055" and of about 0.025" between the rails. FIG. 6I shows a railed square plate 148, including an elongated section 150, upon which are disposed a plurality of rails 152. The railed square plate 148 includes a plurality of fastener openings 154 disposed at the corner portions of the railed square plate 148. A typical railed square plate 148 has a width of about 0.546", a length (l) of about 0.546" and a height at the rails of about 0.055" and of about 0.025" between the rails. FIG. 6J illustrates a large railed triangle 156, including an elongated section 158 upon which are disposed a plurality of rails 160. A large railed triangle 156 includes a plurality of fastener openings 162, located at the corner portions of the triangle shape. A typical large railed triangle plate 156 has a width of about 0.834", a length (l) of about 0.978" and a height at the rails of about 0.055" and of about 0.025" between the rails.

Figure 6K:
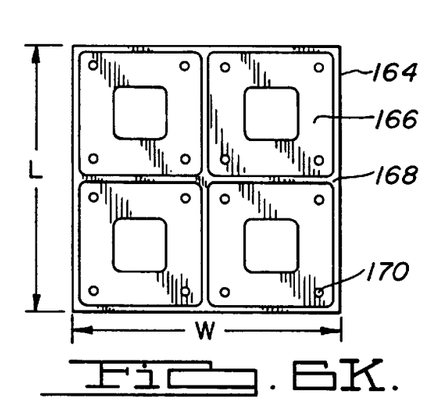
FIG. 6K is a top view illustrating a railed grid osteosynthesis plate according to the teachings of a preferred embodiment of the present invention.
Figure 6L:
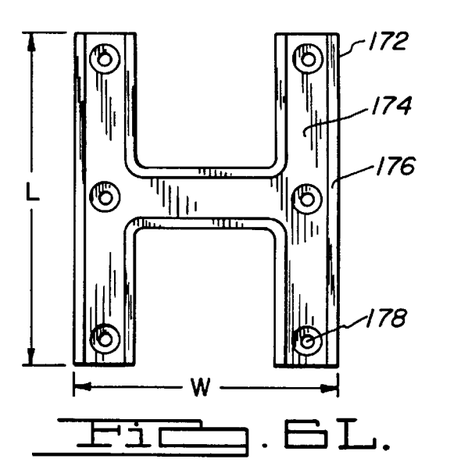
FIG. 6L is a top view illustrating a railed H-osteosynthesis plate with fastener opening countersinks according to the teachings of a preferred embodiment of the present invention.

Referring now to FIG. 6K, there is shown a railed grid plate 164 having at least one elongated section 166 upon which is disposed a rail grid 168. The railed grid plate 164 includes a plurality of fastener openings 170 disposed in a predetermined arrangement upon the railed grid plate 164. A typical railed grid plate 164 has a width of about 1.295", a length (l) of about 1.4" and a height at the rails of about 0.055" and of about 0.025" between the rails. Referring now to FIG. 6L, there is shown a railed H-plate 172 including at least one elongated section 174 upon which are disposed a plurality of rails 176. The railed H-plate 172 includes a plurality of fastener openings 178 which include countersinks disposed at both the terminal and junction locations along the H-shape. A typical railed H-plate 172 has a width of about 1.2261", a length (l) of about 0.830" and a height at the rails of about 0.055" and of about 0.025" between the rails.

It will be appreciated that the examples set forth in FIGS. 6A–6L are meant to be illustrative of the varieties of osteosynthesis plate shapes which may be constructed according to the present invention. It will further be appreciated that these osteosynthesis plates may be constructed of any of the materials previously discussed, or may be constructed from other suitable materials. As before, it is preferred that any of the above osteosynthesis plates be constructed of a bioresorbable material. As before, the bioresorbable material may be combined in a bone stabilization device with bioresorbable surgical fasteners, such as bone screws, or may be combined in a composite bone stabilization device with metallic or metallic alloy surgical fasteners, such as bone screws, of the materials previously discussed.

It will also be appreciated that any of the above osteosynthesis plates may be constructed either in a flat configuration, as shown in FIGS. 2 and 3, or with continuous or discontinuous material projections or protrusions upon their surfaces, which may be in the form of rails as shown in FIGS. 4 and 5, or in other projecting or protruding forms. Additionally, it will be appreciated that any rails provided on the surfaces of these osteosynthesis plates may be discontinuous in the form of broken sections, or may be in an undulating form, either configuration being sufficient for allowing the junction of two or more adjacently disposed osteosynthesis devices upon an underlying bone surface, as previously described.

In the junction of two or more adjacently disposed osteosynthesis devices, it will be appreciated that the overlapping of fastener openings between adjacent plates allows for a single surgical fastener to be inserted through multiple fastener openings, thereby allowing for a linking of adjacent osteosynthesis plates through either a "branching" or a "chain-linking" configuration. It will also be appreciated that two osteosynthesis plates with rails disposed thereon may be joined by placing a single osteosynthesis plate without rails between each of the railed osteosynthesis plates such that the nonrailed osteosynthesis plate partially spans each of the railed osteosynthesis plates.

In addition, it will be appreciated that any of the above osteosynthesis plates may be constructed to include means disposed upon the elongated section to permit the formation of additional fastener openings therethrough during a surgical procedure, as provided in the description relating to FIGS. 2 and 3. Further, all of the above-mentioned osteosynthesis plates are intended to be of a low-profile configuration, whether constructed in a flat configuration, such as in FIGS. 2 and 3, with a rail design, as in FIGS. 4 and 5, or in another configuration, such that a surgical fastener of similarly low-profile may be inserted between adjacent rails, if present, so as not to protrude above the surface of the rails substantially.

As discussed above, the osteosynthesis plates of the present invention in the sense that it returns to its original state are dimensionally stable at the thermochemical state where the osteosynthesis plate is used as well as the thermochemical state in which the osteosynthesis plate may be deformed. The method by which the osteosynthesis plate is formed to have these properties will now be described with reference to FIG. 7. First, a polymer sheet stock is formed at step 180 by compression molding. This step is operable to form a sheet form of the flat plate 50 or the railed osteosynthesis plate 64 with rails 72. This step may also form fastener openings 58 and 74 and countersinks 76. This material is preferably formed with reduced internal stresses to enhance the dimensional stability of the material when being deformed during a surgical procedure at a temperature above the glass transition temperature of the material.

Figure 7:
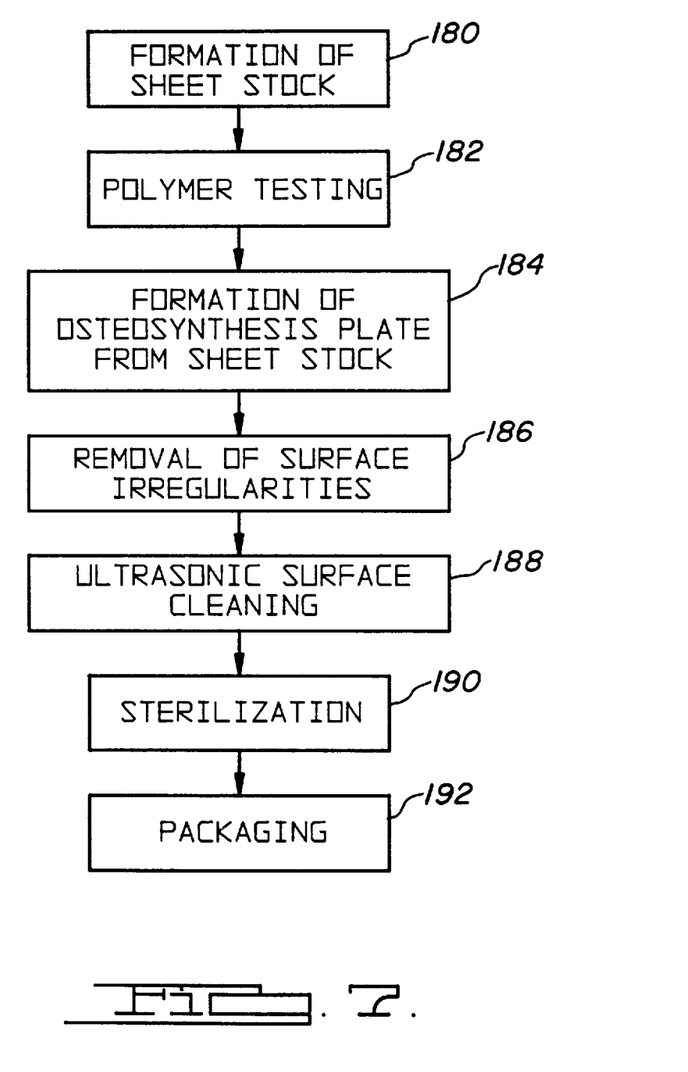
FIG. 7 is a flow chart illustrating the steps of formation of an osteosynthesis plate according to the teachings of a preferred embodiment of the present invention.

In the second step of this method, shown at step 182, the polymer sheet form is tested for such properties as glass transition temperature, inherent viscosity and nuclear magnetic resonance scans for percentage of glyceride as well as determining the crystallinity of the polymer composition using a differential scanning calorimeter. Following the polymer testing step, an osteosynthesis plate, such as flat plate 50 or railed osteosynthesis plate 64, is formed from the sheet stock in step 184 by machining or stamping the fastener openings 58 and 74, the countersinks 76, and rails 72, if these were not part of the original compression molded or extruded stock.

The next step of the method of the present invention involves the removal of surface irregularities at step 186, to enhance a smooth surface and an aesthetic appearance of the article. This is accomplished by trimming with suitable trimming devices, such as knives or cutting blades, or may also be accomplished by an additional stamping step. Once the removal of surface irregularities has occurred, the substantially completed product is subjected to an ultrasonic surface cleaning at step 188. In this step, the outer surface of the osteosynthesis plate is cleaned of fingerprints, soils and oils resulting from contact with human hands and other surfaces, as well as impurities which may collect on the surface. This is accomplished by submerging one or more osteosynthesis plates in a container of isopropanol and submerging in turn this container in a water or aqueous solution ultrasonic bath container and applying ultrasonic waves through the osteosynthesis plate or plates for disengaging surface particulates. This step also includes removing the isopropanol from the surface of the osteosynthesis plates by placing the plates in an evacuation chamber.

In the next step of the method of the present invention, step 190, the osteosynthesis plate is sterilized. Following the sterilization step, the osteosynthesis plate is packaged before sale in step 192. It will be appreciated that the above-mentioned steps of manufacturing an osteosynthesis plate of the present invention may further include additional steps, such as for quality control purposes. These additional steps may include visual or other types of inspections during or between the various steps, as well as final product inspection including additional testing for glass transition temperature, inherent viscosity, nuclear magnetic resonance scans and other quality control testing, such as a three point bending or tensile testing.

The method for enhancing a substantially secured relation between a plurality of adjacent bone portions with reduced bone surface protrusion according to the present invention will now be described. The first step of this method includes providing a low-profile biocompatible osteosynthesis plate, such as the osteosynthesis plate 50 or the osteosynthesis plate 64. The osteosynthesis plate is then positioned upon a plurality of adjacent bone portions. A plurality of surgical fasteners are then provided for enhancing a fixed relation between the osteosynthesis plate and at least one adjacent bone portion. A plurality of surgical fasteners are then positioned within a plurality of fastener openings located upon the osteosynthesis plate. The plurality of surgical fasteners are then secured to the adjacent bone portions, thereby engaging the low-profile biocompatible osteosynthesis plate with each bone portion.

This method may further include the additional steps of creating at least one additional fastener opening through the osteosynthesis plate at a location adjacent to at least one bone portion, positioning an additional surgical fastener within each additional fastener opening, and substantially securing each additional surgical fastener into each bone portion thereby enhancing an engagement of the osteosynthesis plate with each bone portion. This method may also include the step of engaging the osteosynthesis plate with at least one adjacent osteosynthesis plate. In addition, this method may also provide the additional step of deforming the osteosynthesis plate. This may comprise the steps of converting the osteosynthesis plate to a second thermochemical state from a first thermochemical state, shaping the osteosynthesis plate to a first desired configuration, and allowing the osteosynthesis plate to return to the first thermochemical state so as to allow the osteosynthesis plate to retain the first desired configuration. In the situation where the first desired configuration is not sufficient for completing the surgical requirements, the method of the present invention further provides for converting the osteosynthesis plate back to the second thermochemical state thereby allowing the osteosynthesis plate to return to the first configuration, reshaping the osteosynthesis plate to a second desired configuration, and allowing the osteosynthesis plate to return to the first thermochemical state so as to allow the osteosynthesis plate to retain the second desired configuration. In addition, it will be appreciated that the method of the present invention further includes the capability for repetitively converting the osteosynthesis plate to the second thermochemical state, repetitively shaping the osteosynthesis plate to successive desired configurations, repetitively allowing the osteosynthesis plate to return to the first thermochemical state so as to allow the plate to retain successive desired configurations and ceasing converting the osteosynthesis plate to the second thermochemical state when a desired final configuration of the osteosynthesis plate has been achieved.

Alternatively, the method for enhancing a substantially secure relationship between a plurality of adjacent bone portions is similar to that described above, but the osteosynthesis plate 10 is secured by means of an adhesive. In this regard, after the osteosynthesis plate 10 is formed in the manner described above, the surgeon places an adhesive between the bone portions to be secured and the osteosynthesis plate. The adhesive may typically be a cyanoacrylate, though other suitable adhesives may be used. The surgeon then brings the osteosynthesis plate 10 into contact with the bone portions thereby securing the osteosynthesis plate 10 to the bone portions.

The principles of the present invention described broadly above will now be described with reference to the following specific examples, without intending to restrict the scope of the present invention.

EXAMPLE 1

Pellets of a copolymer material comprising about 82% m lactide and about 18% m glyceride are prepared according to the method set forth in U.S. Pat. No. 4,523,591, which is hereby incorporated by reference. The pellets are formed such that they have an inherent viscosity of about 0.96 dl/g and a molecular weight $M_n$ of about 30,000. The inherent viscosity is measured at 30° C. using 62.5 mg. of polymer per 25 milliliters of chloroform. The resulting pellets are approximately 1/16 to 1/8 inches in diameter and have a length of about 1/8 inch.

About 13.5 grams of these pellets are placed into a rectangular mold which is formed with a Teflon base. The interior of the rectangular mold is approximately 4.3×2.25 inches, while the height of the mold is about 0.06 inch. The pellets are placed in the center of the mold such that the center of the pellets is approximately 1 inch high with respect to the base. A Teflon cover is placed over the pellets and then the mold is placed into a vacuum press and evacuated to about −28 inches of Hg. The mold is then heated to approximately 160° C. and a closing force of about 5,000 lbs. is applied to the mold for one minute. The mold is then allowed to cool to a temperature of about 40° C. over a period of about 20 minutes. The Teflon cover of the mold is then removed and the polymer is then removed from the mold. The resulting polymer is then further processed according to the steps shown in FIG. 7 producing a plate having a configuration similar to the plate shown in FIG. 2. The crystallinity of the plate is determined to be less than 10% and is found to have a flex strength of approximately 25,000 psi.

The plate is then placed in a saline solution to determine in vitro the change in flex strength over time as the plate resorbs. After six weeks, the plate is shown to retain about 80% of its flex strength, while the flex strength is approximately zero at about 15 weeks. The plate is completely resorbed after about one year in vivo.

EXAMPLE 2

Pellets of a copolymer material comprising 82% m lactide and 18% m glyceride were prepared in the manner similar to that in Example 1. However, the inherent viscosity of the material was 1.4 dl/g measured at 30° C. using 62.5 mg. of polymer per 25 milliliters of chloroform. The resulting pellets have a molecular weight $M_n$ of about 51,000. The pellets were then used in a manner set forth in Example 1 to produce a number of osteosynthesis plates of the type shown in FIG. 2. Several of the osteosynthesis plates were placed in a saline solution to determine the resorption of the plates over time. The flex strength was initially about 28,000 psi prior to placement in the saline solution and had a crystallinity of less than 10%. After approximately six weeks, the osteosynthesis plate retained about 80% of its flex strength in vitro. The plate was completely resorbed after about one year in vivo.

The remaining osteosynthesis plates were used with skeletally immature rabbits whereby the osteosynthesis plates were placed across the suture lines in the cranium. The scalp was then closed in a normal fashion. Initial post operative examination determined that the plates were not palpable. Subsequent examination of the rabbits showed that there was no growth restriction at six months post operatively, and the area of the skull where the osteosynthesis plates were implanted was excised and there were no gross signs of polymer.

EXAMPLE 3

Pellets of a copolymer material comprising about 82% m lactide and about 18% m glyceride are prepared in the manner set forth in Example 1, though the inherent viscosity is selected to be about 2.0 dl/g measured at 30° C. using 62.5 mg. of polymer per 25 milliliters of chloroform. The resulting pellets have a molecular weight of about 86,500. The pellets are then processed in a manner set forth in Example 1 and the resulting plates are placed in a saline solution to determine strength during resorption. The plates show a retention of 80% of the flex strength at six weeks and lose all their flex strength at 15 weeks. The osteosynthesis plates are completely resorbed after about one year in vivo.

EXAMPLE 4

Pellets of a copolymer material comprising 82% m lactide and about 18% m glyceride are prepared in the manner set forth in Example 1, though the inherent viscosity is selected to be 2.2 dl/g measured at 30° C. using 62.5 mg of polymer per 25 milliliters of chloroform. The resulting pellets have a molecular weight of about 100,000. The pellets are then processed in a manner set forth in Example 1 and the resulting plates are determined to have a crystallinity of less than 10%. The plates are then placed in a saline solution to determine strength during resorption. The plates show retention of about 80% of the flex strength at six weeks and lose all their flex strength at fifteen weeks. The osteosynthesis plates are completed resorbed after about one year in vivo.

While the above description discusses a preferred embodiment of the present invention, it will be understood that the description is exemplary in nature and is not intended to limit the scope of the invention. For example, the device used in the present invention may be of a biocompatible or bioresorbable material. Also, the deformability characteristics of the device may be altered by changes in thermochemical condition of the device, such as exposure to one or more chemical compounds which react with the implant material so as to render it temporarily deformable prior to implantation. It will be appreciated that all of the above steps of the method of the present invention may be associated with any configuration of the osteosynthesis plates previously described. The present invention will therefore be understood as susceptible to modification, alteration and variation by those skilled in the art without deviated from the scope and meaning of the following claims.

What is claimed is:

1. A biocompatible osteosynthesis plate operable to be secured by at least one fastener through at least one fastener opening formed in the plate to a plurality of bone portions, the osteosynthesis plate comprising:

an elongated section having first and second surfaces, the plate being formed from a material, said material being capable of demonstrating a first thermochemical state and a second thermochemical state, said material being more resistant to flexing at said first state than at said second state, said material being dimensionally stable when at said first and second thermochemical states; and means disposed on said elongated section to permit the formation of at least one fastener opening therethrough during the surgical procedure at a plurality of different positions, whereby said biocompatible osteosynthesis plate may be secured to the bone portions by forming said one fastener opening and inserting said one fastener through said one fastener opening into said one of the plurality of bone portions.

2. A bone stabilization device for stabilizing adjacent bone portions, the bone stabilization device comprising:

a biocompatible osteosynthesis component capable of demonstrating at least a first thermochemical state and a second thermochemical state, said component being more resistant to flexing at said first state than at said second state, said component being substantially dimensionally stable when at said first thermochemical state and said second thermochemical state; and means for attaching said component to the adjacent bone portions.

3. The bone stabilization device according to claim 2, wherein said component is deformable along three mutually perpendicular axes.

4. The bone stabilization device according to claim 2, wherein said means for attaching comprises a plurality of surgical fasteners being operable to secure said biocompatible osteosynthesis component to the adjacent bone portions.

5. The bone stabilization device according to claim 2, wherein said biocompatible osteosynthesis component includes a first surface and a second surface and wherein said means for attaching comprises a plurality of fastener openings formed between said first and second surfaces.

6. The bone stabilization device according to claim 5, wherein at least one of said fastener openings includes a recessed portion to receive one of said surgical fasteners.

7. The bone stabilization device according to claim 2, wherein said biocompatible osteosynthesis component includes means for enhancing structural rigidity.

8. The bone stabilization device according to claim 7, wherein said means for enhancing structural rigidity comprises at least two rail sections.

9. The bone stabilization device according to claim 2, wherein said biocompatible osteosynthesis component is at a first configuration at said first thermochemical state and is operable to be deformed to a second configuration at said second thermochemical state.

10. The bone stabilization device according to claim 2, wherein said biocompatible osteosynthesis component is bioresorbable.

11. The bone stabilization device according to claim 2, wherein said biocompatible osteosynthesis component comprises between about 70–85% lactide and between about 15–30% glyceride.

12. The bone stabilization device according to claim 2, wherein said biocompatible osteosynthesis component has a molecular weight of less than about 100,000.

13. A bioresorbable biocompatible osteosynthesis plate operable to be secured to a plurality of bone portions during a surgical procedure, the osteosynthesis plate comprising:
a section having a first dimension and a second dimension and wherein said first dimension is greater than about six times said second dimension of a portion of said section.

14. The bioresorbable biocompatible osteosynthesis plate of claim 13, the plate being formed from a material having a glass transition temperature, said material being substantially dimensionally stable at said glass transition temperature.

15. A method for securing adjacent bone portions using a biocompatible osteosynthesis component, said method comprising the steps of:
forming the biocompatible osteosynthesis component, said step of forming the component including:
(a) providing a material that is capable of demonstrating at least a first thermochemical state and a second thermochemical state, said material being more resistant to flexing at said first state than at said second state, said material being substantially dimensionally stable when at said first thermochemical state and said second thermochemical state, and
(b) forming said material into the biocompatible osteosynthesis component; and
securing the biocompatible osteosynthesis component to the adjacent bone portions.

16. The method for securing adjacent bone portions of claim 15, wherein the component defines a plate having a first surface and a second surface and wherein said step of securing the biocompatible osteosynthesis component includes the step of forming at least one opening between said first and second surfaces after formation of said plate.

17. The method for securing adjacent bone portions of claim 15, wherein said step of securing the biocompatible osteosynthesis component to the adjacent bone portions includes the step of disposing an adhesive between the biocompatible component and the adjacent bone portions.

18. The method for securing adjacent bone portions of claim 17, wherein said adhesive is a bioresorbable cyanoacrylate.

19. The method for securing adjacent bone portions of claim 15 wherein said component has a temperature, including the step of deforming said biocompatible osteosynthesis component after elevating said temperature of said component.

20. The method for securing adjacent bone portions of claim 19, wherein said biocompatible osteosynthesis component has a shape, said shape defining a first configuration, said step of deforming said component comprising the steps of:
converting said biocompatible osteosynthesis component from said first thermochemical state to said second thermochemical state;
changing the shape of said biocompatible osteosynthesis component from said first configuration to a second configuration; and
allowing said biocompatible osteosynthesis component to return to said first thermochemical state thereby allowing said biocompatible osteosynthesis component to retain said second configuration.

21. The method for securing adjacent bone portions of claim 19, wherein said step of deforming said biocompatible osteosynthesis component comprises the steps of:
(a) converting said biocompatible osteosynthesis component to said second thermochemical state from said first thermochemical state;
(b) changing the shape of said biocompatible osteosynthesis component while at said second thermochemical state;
(c) allowing said biocompatible osteosynthesis component to return to said first thermochemical state; and
(d) repeating steps (a) through (c) until a desired configuration of said biocompatible osteosynthesis component is obtained.

* * * * *

UNITED STATES PATENT AND TRADEMARK OFFICE
CERTIFICATE OF CORRECTION

PATENT NO. : 5,868,746
DATED : February 9, 1999
INVENTOR(S) : Sarver, et al.

It is certified that error appears in the above-indentified patent and that said Letters Patent is hereby corrected as shown below:

Column 2, line 40, glyceride should be --glycolide--.

Column 2, line 49, "106" should be $10^6$--.

Column 13, line 50 "1.2261" should be --1,226--.

Signed and Sealed this

Tenth Day of April, 2001

Attest:

NICHOLAS P. GODICI

*Attesting Officer*    Acting Director of the United States Patent and Trademark Office